United States Patent [19]

Moorehead

[11] Patent Number: 5,389,091
[45] Date of Patent: Feb. 14, 1995

[54] SITE-SELECTIVE DURABILITY-ENHANCED CATHETER AND METHODS OF MANUFACTURING AND USING SAME

[75] Inventor: H. Robert Moorehead, Salt Lake City, Utah

[73] Assignee: C. R. Bard, Inc., Murray Hill, N.J.

[21] Appl. No.: 6,435

[22] Filed: Jan. 15, 1993

Related U.S. Application Data

[63] Continuation-in-part of Ser. No. 665,787, Mar. 7, 1991, abandoned.

[51] Int. Cl.$^6$ ............................................. A61M 25/00
[52] U.S. Cl. ..................................... 604/282; 604/273
[58] Field of Search .................. 604/93, 264, 280–283; 606/191, 194; 128/656, 658; 138/124–126, 174

[56] References Cited

U.S. PATENT DOCUMENTS

| | | | |
|---|---|---|---|
| 2,308,484 | 1/1943 | Auzin et al. | 18/58 |
| 2,739,616 | 3/1956 | Duff | 138/56 |
| 3,010,194 | 11/1961 | Fratzke | 29/235 |
| 3,426,744 | 2/1969 | Ball | 128/1 |
| 3,485,234 | 12/1969 | Stevens | 128/2 |
| 3,630,207 | 12/1971 | Kahn et al. | 128/350 R |
| 4,291,454 | 9/1981 | Sawaryn | 29/426.6 |
| 4,425,919 | 1/1984 | Alston, Jr. et al. | 128/658 |
| 4,431,031 | 2/1984 | Ettlinger | 138/124 |

(List continued on next page.)

FOREIGN PATENT DOCUMENTS

| | | | |
|---|---|---|---|
| 0125844 | 11/1984 | European Pat. Off. | A61M 25/00 |
| 0263645 | 4/1988 | European Pat. Off. | A61M 25/00 |
| 0274129 | 7/1988 | European Pat. Off. | A61M 25/00 |

OTHER PUBLICATIONS

D. Aitken, et al., "The 'Pinch–Off Sign': A Warning of Impeding Problems With Permanent Subclavian Catheters", 148 AM. J. Surgery 633–36 (1984).

T. Franey, et al., "Catheter Fracture and Embolization in a Totally Implanted Venous Access Catheter", 12 J. Parenteral and Enteral Nutrition 528–30 (1988).

(List continued on next page.)

Primary Examiner—C. Fred Rosenbaum
Assistant Examiner—Chalin Smith
Attorney, Agent, or Firm—Workman Nydegger & Seeley

[57] ABSTRACT

The present invention is directed to novel methods and apparatus for structurally enhancing a catheter which can be employed to withstand the damaging stresses experienced by catheters implanted in bodily tissues, particularly catheters implanted in the compressed area between the clavicle and first rib of a patient. The enhanced catheter includes a nonmetallic inner tubular sleeve comprised wholly of a compliant material that is inserted in frictional engagement with the interior of the walls of the catheter. The inner sleeve has an outer diameter greater than the inner diameter of the catheter.

The structurally enhanced catheter can be manufactured by immersing a portion of a catheter in freon which causes the immersed portion to swell to have an inner diameter temporarily greater than the outer diameter of the tubular sleeve. Thereafter, the tubular sleeve is advanced site-selectively to a position within the catheter. Finally, the portions of the exposed catheter are allowed to return to their normal size around the inserted reinforcing sleeve.

Alternatively, the structurally enhanced catheter can be manufactured by advancing a reinforcing sleeve site-selectively to a position within the catheter while the catheter is inflated by introducing pressurized gas. The tubular sleeve is oriented on a hollow rod connected to an air pump and moved to the open end of the catheter. This forces air ahead of and around the tubular sleeve, increasing the diameter of the catheter surrounding the reinforcing sleeve so that the reinforcing sleeve may be advanced. After the reinforcing sleeve is in position, the rod is removed and the catheter returns to its normal position frictionally engaging the exterior of the reinforcing sleeve.

40 Claims, 4 Drawing Sheets

U.S. PATENT DOCUMENTS

| | | | |
|---|---|---|---|
| 4,498,473 | 2/1985 | Gereg | 128/207 |
| 4,547,193 | 10/1985 | Rydell | 604/282 |
| 4,553,959 | 11/1985 | Hickey et al. | 604/247 |
| 4,577,543 | 3/1986 | Wilson | 604/282 |
| 4,676,229 | 6/1987 | Krasnicki et al. | 128/4 |
| 4,690,175 | 9/1987 | Ouchi et al. | 138/131 |
| 4,713,049 | 12/1987 | Carter | 604/282 |
| 4,723,947 | 2/1988 | Konopka | 604/272 |
| 4,748,982 | 6/1988 | Horzewski et al. | 128/344 |
| 4,775,371 | 10/1988 | Mueller, Jr. | 604/280 |
| 4,776,844 | 10/1988 | Ueda | 604/281 |
| 4,817,613 | 5/1989 | Jaraczewski et al. | 604/282 |
| 4,842,590 | 6/1989 | Tanabe et al. | 604/282 |
| 4,875,468 | 10/1989 | Krauter | 138/DIG. 14 |
| 4,899,787 | 2/1990 | Ouchi et al. | 138/131 |
| 4,900,314 | 2/1990 | Quackenbush | 604/282 |
| 4,955,862 | 9/1990 | Sepetka | 604/282 |
| 4,973,319 | 11/1990 | Melsky | 604/247 |
| 4,994,047 | 2/1991 | Walker et al. | 604/280 |
| 5,061,257 | 10/1991 | Martinez et al. | 604/282 |

OTHER PUBLICATIONS

J. Noyen, et al., "Spontaneous Fracture of the Catheter of a Totally Implantable Venous Access Port: Case Report of a Rare Complication", 5 J. Clinical Oncology 1295-99 1987).

R. Rubenstein, et al., "Hickman Catheter Separation", 9 J. Parenteral and Enteral Nutrition 754-57 (1985).

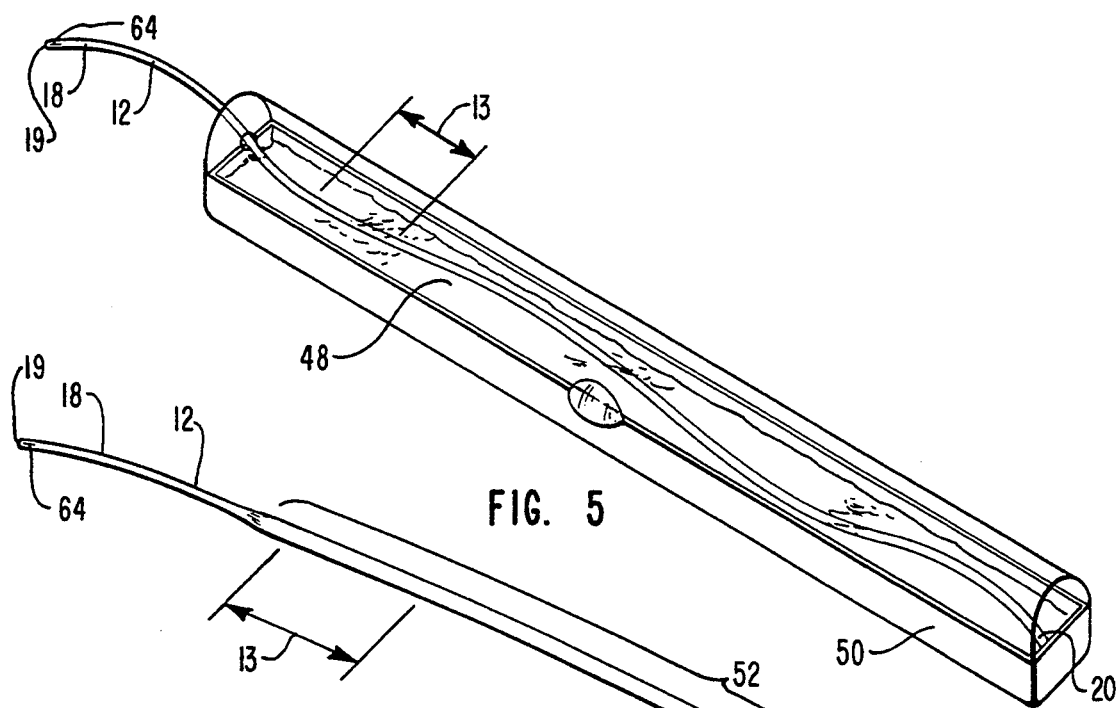
FIG. 5
FIG. 6
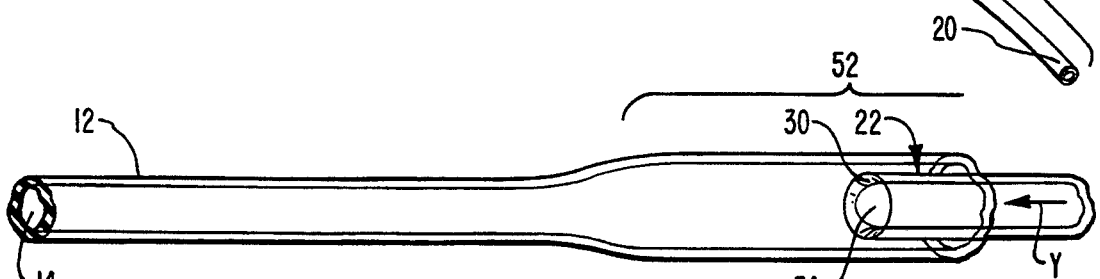
FIG. 7
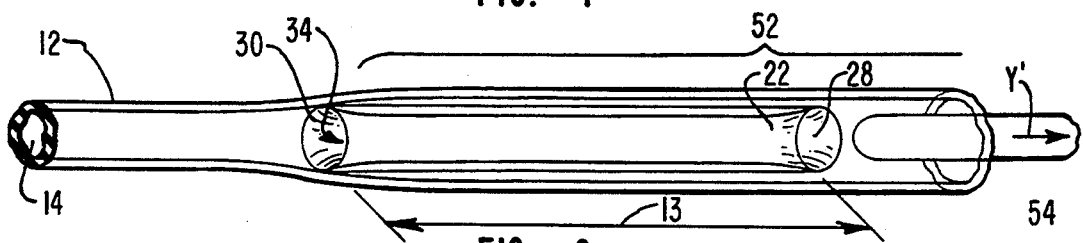
FIG. 8
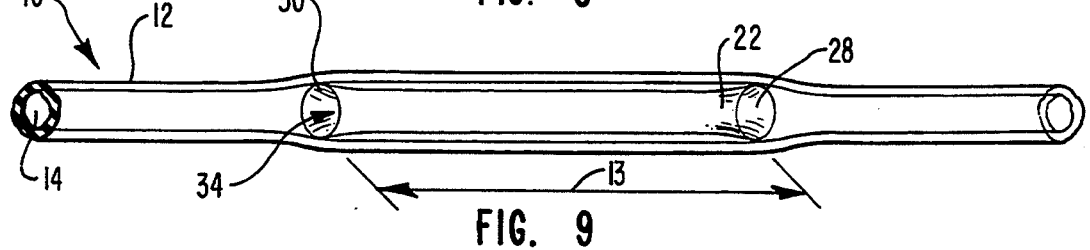
FIG. 9

SITE-SELECTIVE DURABILITY-ENHANCED CATHETER AND METHODS OF MANUFACTURING AND USING SAME

RELATED APPLICATIONS

This application is a continuation-in-part application of U.S. patent application Ser. No. 665,787, which was filed on Mar. 7, 1991, now abandoned in the name of H. Robert Moorhead for an invention then entitled SITE-SELECTIVE REINFORCED CATHETER AND METHODS OF MANUFACTURING AND USING THE REINFORCED CATHETER.

BACKGROUND

1. Field of the Invention

The present invention relates to methods and apparatus for the site-selective enhancement of a catheter which, when installed in the body of a patient, is subjected to potentially damaging stresses due to body movement. In particular, the present invention relates to a method and apparatus for enhancing the durability of such portions of a soft, medical-grade silicone rubber catheter as become implanted on a long-term basis in an area of the body subjected to repeated intermittent compressive or abrasive forces. One example of such an area is the so-called "pinch-off region" located between the clavicle and first rib, a region traversed by a central venous access catheter installed by way of the percutaneous subclavian route.

2. Background Art

Patients undergoing long-term intravenous therapy have benefited from use of indwelling central venous access catheters. The distal tip of such a catheter is entered into the cardiovascular system at a peripheral puncture site and then threaded therefrom through the cardiovascular system along a convoluted pathway to a region of high volume blood flow and turbulence near the heart, such as in the superior vena cava. Thusly positioned, the central venous access catheter remains resident for a period of time ranging from a few weeks to more than two years. During that entire residency, the catheter is agitated within the cardiovascular system seventy to eighty times per minute by the pulsating fluid flow therein produced by the action of the heart. This can rapidly produce erosion of the blood vessels wherever contact is effected by the catheter. Maximum dangers arise at bends in the cardiovascular system and at the distal tip of the catheter. In order to overcome this problem and permit the long-term implantation of central venous access catheters, such catheters are made of a soft biocompatible material, such as a medical-grade silicone rubber. It has been found that this material avoids irritating or eroding the passage ways of the cardiovascular system over long implantation periods. Once thusly implanted, such catheters have generally proven effective for the purpose of infusing chemotherapeutic drugs and antibiotics, conducting intervenous feeding, providing access for withdrawing blood samples, as well as affording access to the central venous system for any other purposes.

Nonetheless, since the introduction of indwelling central venous access catheters, a relatively constant but low level of use-related complications have been recorded relative thereto.

One group of such use-related complications is associated with indwelling central venous access catheters that are installed along pathways that traverse regions in the body subjected on a regular basis to repeated intermittent compressive or abrasive forces. In general, such stresses impose problems of long-term local wear on an implanted catheter made of a soft biocompatible material, such as silicone rubber. In such catheters repeated intermittent compressive or abrasive forces can result initially in a breech of the integrity of the lumen of the catheter at the region of wear. This in turn leads to leakage of the infusate at that point and the destruction of tissue local thereto.

Once a central venous access catheter is weakened at such a region of wear, it may even be impossible to extract the catheter in an intact condition, as such catheters are removed by pulling them out of the cardiovascular system by drawing on the proximal end thereof. In this process, a weakened catheter is likely to snap at its point of weakening leaving the distal portion of the catheter in the body of the patient.

If the catheter is not removed, however, continued local wear of an implanted venous access catheter can lead to a total severance of the catheter at the point of wear. The distal portion of the catheter is then free to migrate through the cardiovascular system raising all the risks attendant thereto. In the meantime, if undetected, the severed catheter continues in addition to emit infusate at the point of severance, instead of at a proper location with high volume blood flow and turbulence.

The problem of indwelling central venous catheter puncture or pinch-off due to compressive and abrasive forces in the body is particularly acute during the residence in the body of catheters installed along a route currently preferred by most medical professionals. This is the percutaneous subclavian route of installation, which traverses a so-called "pinch-off region" between the clavicle and first rib. Normal movement of the patient causes these two bones to closely approach each other, compressing the tissue and any catheter located therebetween. The tissue in the "pinch-off region" has adapted to these facts of anatomy and is not injured by such movement. An indwelling catheter, however, is subjected to repeated compression and abrasion, which in a predictable number of instances results in complications which have been suggested above and have been described in detail in medical literature to be cited below.

Preliminarily, however, the reader is referred to FIG. 1, which illustrates the internal anatomical features which result in repeated intermittent catheter compression and abrasion in this particular "pinch-off region" of the body. FIG. 1 is designed to assist the reader in comprehending the source of the problem of catheter failure from the action of the body in the "pinch-off region," as well as the inadequacy of efforts to date to deal with those failures. It should be understood, however, that other regions of the body traversed by long-term implantable catheters could be subjected to similar compressive and abrasive forces, and thus produce the risks associated therewith.

In FIG. 1, the upper right torso of the skeletal system and selected cardiovascular passageways of a patient are illustrated. There, right first rib A and left first rib B can be seen to be connected at the forward ends thereof by ligaments C and D, respectively, to the sternum E. The rearward ends of first rib A and second rib B are attached to a vertebrae F of the patient. Second right rib G and second left rib H are also shown for the purpose of added perspective. Each are connected at the forward ends thereof to sternum E and at the rearward ends to a vertebrae I shown below and adjacent to vertebrae F. A portion of right second rib G has been broken away in FIG. 1 in order to illustrate the superior vena cava J free of any frontal obstruction.

Also shown among the skeletal system illustrated in FIG. 1 is the right clavicle K and left clavicle L, which are each attached at the medial ends thereof by a ligament M to the top of sternum E. At the end of right clavicle K remote from sternum E, FIG. 1 includes portion of the right humerus N and right scapula O located adjacent thereto. A vertebrae Q above and adjacent to vertebrae F is also illustrated.

FIG. 1 includes with the skeletal elements just described selected components of the cardiovascular system of the patient. There the right axillary subclavian vein R can be seen to be a blood vessel returning blood from the right arm of the patient toward the heart. Axial subclavian vein R extends in the direction of that return blood flow between right clavicle K and right first rib A, thereafter to be denominated the right subclavian vein S. The external jugular vein T and the internal jugular vein U join subclavian vein S, which turns downwardly into superior vena cava J.

Normal body movements by the patient bring right clavicle K into close proximity to right first rib A regularly but intermittently, compressing therebetween axillary subclavian vein R and the tissue in the vicinity thereof. This is the area referred to with notoriety as the "pinch-off region".

The intermittent compression of the "pinch-off region" does not have adverse consequences for axillary subclavian vein R. The name attributed to the "pinch-off region" arises from the effect of the intermittent compressive and abrasive forces imposed by that region on any catheter introduced into superior vena cava J by way of being disposed in or being disposed parallel to the exterior of axillary subclavian vein R. A catheter disposed along either routes necessarily passes through the "pinch-off region". Such a catheter V is also shown in FIG. 1.

Catheter V can been seen to have been entered into the cardiovascular system of the patient at a puncture site W in axillary subclavian vein R. Catheter V extends therefrom toward the heart of the patient through the balance of the axillary subclavian vein R, through subclavian vein S, and into superior vena cava J. There the distal tip X of catheter V is intended to reside on a long-term basis. Superior vena cava J is a region of high volume blood flow and turbulence in which it is appropriate for infusate to be introduced from distal end X of catheter V. The route of insertion described above is referred to as the percutaneous subclavian route of insertion.

A catheter, installed by way of the percutaneous subclavian route can enter the cardiovascular system other than at a puncture site such as puncture site W, which is located outside of the "pinch-off region" toward the right arm. The catheter may pass through the "pinch-off region" subcutaneously, parallel to and on the exterior of the axillary subclavian vein R, thereby to actually enter the cardiovascular system at a puncture site in the subclavian vein located medial of the "pinch-off region". Nevertheless, such a catheter does not avoid the intermittent compressive and abrasive forces arising from natural body movement in the "pinch-off region". Accordingly such a catheter is also susceptible to the problems of wearing and severance discussed above.

Despite the risks of catheter wear and catheter pinch-off associated with the subclavian route of insertion for an indwelling intravenous catheter, that route of insertion is generally preferred relative to alternate routes of insertion, or to forgoing the therapeutic opportunities presented by the use of an indwelling central venous access catheter.

Below four (4) articles of medical literature will be described which report on the adverse consequences resulting to patients with indwelling catheters that traverse the "pinch-off region" illustrated in FIG. 1. Each of the four (4) articles is specifically incorporated herein by reference.

The first of these articles of medical literature is D. Aitken, et al., "The 'Pinch-Off Sign': A Warning of Impending Problems With Permanent Subclavian Catheters", 148 AM. J. SURGERY 633–36 (1984). In this article four (4) instances of complications are reported that resulted from the passage of a central venous Hickman and Broviac catheter between the clavicle and the first rib in patients requiring long-term venous access for home parenteral nutrition, frequent blood sampling, or the delivery of medication, such as chemotherapy for cancer. In one instance, catheter transection occurred at the clavicle resulting in the distal catheter segment becoming coiled in the mediastinum. The anatomy of the "pinch-off region" is explored in this article in some detail.

The second article is T Franey, et al., "Catheter Fracture and Embolization in a Totally Implanted Venous Access Catheter", 12 J. PARENTERAL AND ENTERAL NUTRITION 528–30 (1988). Reported there is the case of a totally implanted venous access system placed for chemotherapy in the body of a 24-year-old male patient with Hodgkins disease for chemotherapy. Twelve (12) months after the implantation it was noted on a chest x-ray that the catheter had fractured and that the distal fragment had embolized to the right ventricle. In the article catheter separation and embolization is stated to be a recognized but uncommon complication with Hickman catheters, as well as with other implanted central venous catheters. With the increasing use of such venous access systems, the article forecasts that these complications will become more prevalent.

The third article of medical literature is J. Noyen, et al., "Spontaneous Fracture of the Catheter of a Totally Implantable Venous Access Port: Case Report of a Rare Complication", 5 J. CLINICAL ONCOLOGY 1295–99 (1987). There the case of the spontaneous fracture of the outlet catheter of a totally implantable venous access port (IVAP) is presented. Thirty-seven (37) weeks after implantation, the outlet catheter was broken at the entrance into the left subclavian vein. The distal part was embolized in the left pulmonary artery. The embolized remnant was retrieved in an outpatient setting, using a grasping forcipal catheter through a 7 French long-sheath. Experimental study of the catheter revealed that it had been broken due to a local cause, probably the longstanding compression at the narrow space between clavicle and first rib. The article emphasizes the need accordingly to ascertain the position and intactness of the outlet catheter employed with an IVAP before using that system to infuse cytostatic agents.

Finally is the article, R. Rubenstein, et al., "Hickman Catheter Separation", 9 J. PARENTERAL AND ENTERAL NUTRITION 754–57 (1985). There, seven (7)

patients with Hickman/Broviac catheters implanted by the percutaneous subclavian route are reported to have had catheter separation and embolization. One catheter implanted through the cephalic vein cutdown was also separated. The method of percutaneous subclavian catheter insertion is briefly described, and the mechanism of catheter separation is discussed. Along percutaneous insertion routes between the clavicle and first rib, the body produces compressive and shearing force which can cause the silicone catheter to break-after several months. Embolized catheter fragments must be retrieved with a percutaneous transfemoral venous snare. The described complication represents a 1% incidence. Recommendations to deal with or minimize this problem mentioned in the article include chest X-rays every 2 to 3 months to identify catheter indentation at the thoracic inlet, and early removal of catheters for patients with radiologic evidence of significant catheter compression.

In summary research has indicated that the probable cause of most reported partial separations and total separations of implanted catheters in the "pinch-off region" is due to longstanding intermittent compression and abrasion of the catheter at the narrow space between the clavicle and first rib. Movement of the shoulder draws the clavicle into close proximity against the first rib exposing a catheter therein disposed to a pincher-like pressure and to repeated compressing, grinding, and rubbing. This causes the weakening that results in partial or total catheter separation.

Partial separation of the catheter can lead to various complications, the most important of which is that a hole in the catheter wall will allow the exit of infusates at an undesired location. Some infusates are extremely toxic, and the leakage thereof has required surgery to be performed to remove pockets of resulting dead tissue around the leak site.

The partial separation of a catheter can eventually progress to the separation of the catheter into two parts due to continued compression and abrasion. This results in various other complications, such as embolization. With blood flow to propel the separated distal end of the catheter, this severed portion of the catheter almost always ends up in the pulmonary vessels leading from the right ventricle to the lungs. Surgical procedures are indicated in such an event, and these result in trauma to a patient, both mentally and physically.

As mentioned above, implantable catheters of this type must be compliant due to the disposition of the catheter in relatively soft layers of tissue, including in particular the vessels of cardiovascular system. Flexibility in the catheter prevents unnecessary irritation of tissue layers and also enables the catheter to be routed through the bends in blood vessels. The effects of the imposition of compressive and abrasive forces on the soft material structure of such catheters, however, gives rise to the complications discussed above related to catheters inserted through the percutaneous subclavian route.

Efforts to solve the problem of catheter wear and catheter pinch-off have been attempted. It has been noted that the compression of the catheter may be alleviated by having patients lie supine with the arm and shoulder slightly raised. For obvious reasons, it cannot be suggested that a patient maintain such a position indefinitely. Such a procedure would require a major deviation from currently existing standard practices and would impose significant and difficult patient handling problems on medical personnel. Hence, for long-term indwelling catheters, this is not an adequate solution.

Alternately, it has been suggested to consider utilizing catheter implantation through a jugular vein, such as internal jugular vein U illustrated in FIG. 1. While use of the internal jugular vein will avoid exposing the catheter to the "pinch-off region" between the clavicle and the first rib, the entry of a catheter into a jugular vein cannot be accomplished by a percutaneous insertion. Rather, use of the jugular vein route requires a cut-down procedure, which ultimately ruins the jugular vein for any subsequent circulatory functions. Thus, this method of avoiding the risks of the "pinch-off region" requires a patient to accede to the permanent loss of a healthy jugular vein.

Alternately, it has been proposed to interweave metallic substances or other stress resistant materials in the wall of the catheter to counteract the stress imposed thereon by the body of the patient. Unfortunately, if the catheter is noncompliant or is relatively stiff, it cannot undergo easy flexing. Then the catheter is likely to irritate or damage the relatively soft layers of tissue which surround it. Again, this is an inadequate response for long-term indwelling catheters.

It has also been proposed to increase the thickness of the catheter wall in the region of anticipated wear or to mold a layer of a pliable material over the entire length of a catheter. Any measure which substantially increases the outer diameter of the catheter, however, will require enlargement of the instruments by which that catheter is inserted into the cardiovascular system. Whether the enlarged diameter is local to the region of anticipated wear or effected over the entire length of the catheter, enlarged instruments for insertion will invariably increase the trauma and seriousness of the procedures by which the catheter is inserted.

In addition, thickening the catheter, particularly over the entire length thereof, would increase the torsional rigidity of the catheter. For reasons previously set forth, such a procedure would result in a noncompliant and relatively stiff catheter which could irritate body tissues and erode areas of vital organs of the body, such as the blood vessels, where the catheter comes in contact with such organs.

BRIEF SUMMARY AND OBJECTS OF THE INVENTION

The present invention seeks to resolve problems incident to percutaneously placed catheters that are subjected to potentially damaging stresses due to body movements. More specifically, the apparatus and method of this invention constitute an important advance in the enhancement of the durability of catheters made of soft, medical grade, silicone rubber, where such catheters are to be disposed traversing the "pinch-off region" between the clavicle and first rib of a patient, as when a catheter is implanted by way of the percutaneous subclavian route of insertion. Other regions of the body can present similar risks to implanted catheters and are accordingly within the scope of the problem addressed by the present invention.

One object of the present invention is, accordingly, to provide an apparatus and method for enhancing the durability a percutaneously placed catheter that is to be disposed in or traversing an area of the body of a patient that is subject to damaging stresses due to body movement.

An additional object of the present invention is to reduce the susceptibility of catheters implanted by way of the percutaneous subclavian route to the damaging effects of compressive forces imposed on the catheter by the body.

Also, it is an object of the present invention to prevent damage to the lumen in implanted catheters and the associated risks to the patient by eliminating the partial or total separation catheters at the portions thereof traversing areas of the body that are subject to damaging stresses due to body movement.

Additionally, it is an object of the present invention to provide a catheter as described above as will have the capacity to be installed, used, and removed without major deviation from currently existing standard practices.

Another object of the present invention is to provide an apparatus and method for enhancing a percutaneously placed catheter to achieve the above objects and maintain adequate catheter softness to easily follow the normal insertion path for such a catheter and to avoid irritating or eroding the tissue of the cardiovascular system during periods of prolonged implantation.

Still a further object of the present invention is to provide a percutaneously placeable catheter as described above which leaves the patient in which it is implanted free to engage in normal movement.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

Briefly summarized, the foregoing objects and advantages are realized by the apparatus and method of the present invention, wherein a structural enhancement having specific physical properties is placed in an area of a catheter that is subject to potentially damaging stresses due to body movement. The enhancement in the structure of the catheter increases it durability in the fore of such stresses, but is not an enhancement to the structure of the catheter that renders the catheter rigid or inflexible in the portion thereof subjected to these stresses. Therefore, the catheter with the structural enhancement can easily follow and reside in the normal insertion path of the catheter in the body of the patent without injuring body tissues therealong.

The structured enhancement comprises a flexible nonmetallic inner tubular sleeve made wholly of a biocompatible material that will not become worn by sustained intermittent compressive and abrasive body forces. Nonetheless, the inner sleeve does not resist those forces, as it is made of a material that is flexible and will closely follow the normal insertion path of the catheter through the body of the patient. One such material is polyurethane. The inner sleeve has an outer diameter greater than the inner diameter of the catheter. It is inserted selectively to a desired location within the catheter tube and maintained there by frictional engagement of the inner walls of the catheter tube. In one embodiment, the tubular sleeve has chamfered ends which conform the tubular sleeve to the configuration of the inside of the catheter in which it resides. This allows fluids to travel unhindered in the catheter and through the tubular sleeve.

The inner sleeve is selectively positioned at the point corresponding to the regions of stress anticipated to be imposed on the catheter by the body of the patient. In the case of indwelling central venous access catheters to be inserted by the subclavian route, this point corresponds to the portion of the catheter anticipated to traverse the "pinch-off region" between the first rib and clavicle. It should be pointed out, however, that the foregoing is an example of a point to which such an inner sleeve may be inserted and is not meant to limit the scope of areas in the body of a patient in which the inventive catheter may be employed.

The outer diameter of the reinforcing inner sleeve is slightly larger than the inner diameter of the catheter. Thus, when the reinforcing inner sleeve resides within the catheter, the catheter presses and frictionally engages the exterior of the reinforcing inner sleeve. In spite of any degradation or separation of the catheter tube from compressive or abrasive body forces, the inner sleeve remains intact.

The inner sleeve will therefore, continue to maintain a connection between even severed portions of a catheter because the severed portions continue to remain in frictional engagement with the reinforced sleeve. Thus, the inventive catheter can be used for long periods of time without leakage, even if there is a partial separation or total separation of the catheter wall.

By this structural arrangement, the leakage of infusates through any partial separation in the catheter wall is prevented. Likewise, the possibility of total catheter separation is prevented.

Two methods are disclosed herein for the manufacture of the inventive catheter: (1) the "chemical soak" method, and (2) the "pressurized gas" method. Other additional methods may be applicable thereto.

In the "chemical soak" method, the catheter is immersed in a material, such as freon, which causes silicone to swell. The inner sleeve is placed on a rod and abutted against an encircling push ring. The rod and inner sleeve are then advanced into the catheter to the position desired, whereupon the rod is withdrawn. Thereafter, when the portions of the catheter exposed to freon are dried, the catheter returns to its original size, and the inner sleeve is trapped in the lumen of the catheter.

In the "pressurized gas" method air at a high pressure and controlled volume is utilized to partially inflate the catheter and at the same time to provide a nontoxic, low-friction interface between the polyurethane inner sleeve and the inner surface of the catheter.

The catheter is soft-clamped at a position intermediate the desired reinforcement site and any distal opening to the lumen therein. The inner sleeve is placed on a hollow rod, such as a needle cannula, and abutted against an encircling push ring. The end of the hollow rod remote from the inner sleeve is connected to a low-volume, high pressure air source by an air line. The end of the push rod with the inner sleeve mounted thereon is entered to and advanced along the lumen of the catheter from the open proximal end thereof. The pressurized air passing through the hollow rod and inner sleeve inflates and slightly enlarges the distal end of the catheter and escapes therefrom between the advancing inner sleeve and the inner wall of the catheter. As a result, the sleeve and push rod are easily advanced into position, whereupon the rod is withdrawn from the inner sleeve and the catheter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are therefore not to be considered limiting of its scope, the invention will be described with additional specificity and detail through the use of the accompanying drawings in which:

FIG. 5 is a perspective view of all initial step of the "chemical soak" method of the present invention to produce the inventive catheter in which a catheter tube is treated with a chemical;

FIG. 6 is a perspective view of the catheter of FIG. 5, after it has been treated with a chemical in the "chemical soak" method of the present invention;

FIG. 7 is a side view of a succeeding step of the "chemical soak" method of the present invention in which the inner sleeve is inserted along the enlarged portion of the catheter illustrated in FIG. 6;

FIG. 8 is a side view of a succeeding step of the "chemical soak" method of the present invention in which the rod of FIG. 7 is being retracted from the catheter lumen after insertion of the inner sleeve thereinto;

FIG. 9 is a side view of the inventive catheter produced by the "chemical soak" method of the present invention in which the catheter of FIG. 8 has been dried;

DETAILED DESCRIPTION OF THE PREFERRED EMBODIMENTS

The present invention can be best understood by reference to the drawings, wherein like parts are designated with like numerals throughout.

Figure 1:
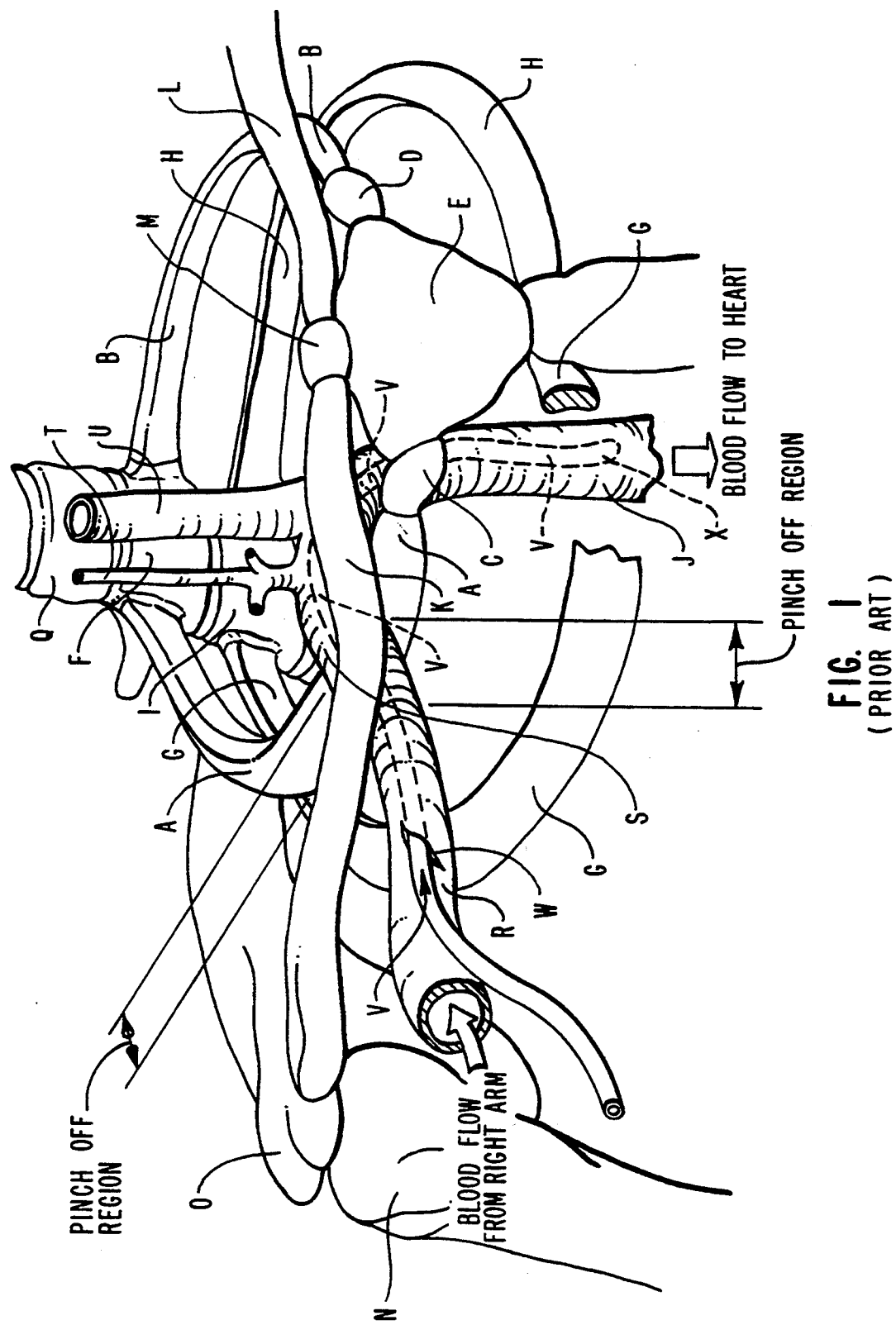
FIG. 1 is a perspective view of selected internal skeletal and cardiovascular anatomical features of the upper right torso of the body of a patient designed to illustrate the "pinch-off region" associated with the percutaneous subclavian route of catheter insertion.

The apparatus of the present invention can be understood with reference to FIG. 1, which illustrates an inventive catheter 10 incorporating teachings of the present invention. As inventive catheter 10 is structurally enhanced at a selected region thereof, inventive catheter 10 will be commonly referred to in this application as being "reinforced." Nevertheless, as will be apparent from the disclosure below of the materials which comprises the constituent elements of inventive catheter 10, inventive catheter 10, even in the selected region of structural enhancement thereof, is a flexible structure capable of yielding upon the application thereto of compressive or torsional stresses. Therefore, catheter 10 can easily follow and reside in the normal insertion path in the body of a patient without causing injury to body tissues therealong.

Inventive catheter 10 comprises a catheter tube 12 made of a compliant medical grade material with a longitudinal lumen 14 extending through a substantial portion of the length thereof. A region 13 of catheter tube 12 is intended to be subjected to compressive forces when inventive catheter 10 is implanted in the body of a patient.

In one embodiment of the present invention, catheter tube 12 is made from silicone rubber. This type of material is preferred in light of its biocompatible nature. Also, the gentleness to bodily tissues of catheters made from silicone rubber makes this choice of material ideal. Nevertheless, this type of material is but an example of that from which catheters can be constructed, and the present invention is not limited to this choice of material.

Figure 2:
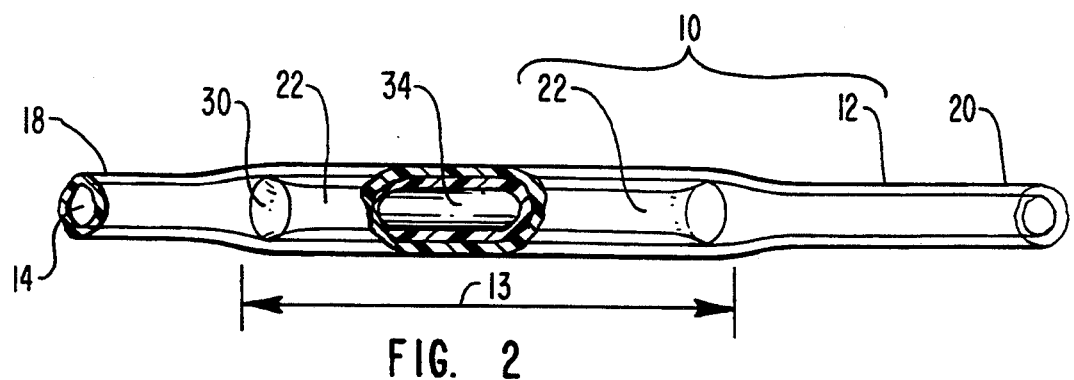
FIG. 2 is a side view in the partial break-away of a preferred embodiment of the inventive catheter.

In the present invention catheter tube 12 may be an indwelling central venous access catheter. Catheter tube 12 is typically percutaneously implanted within a patient for a time period which can range from about ten minutes to about two years. Nevertheless, the present invention includes all types of catheters, and catheter tube 12 is not required to be an indwelling central venous access catheter. Catheter tube 12 can have a single lumen or a plurality of lumens. As illustrated in FIG. 2, however, catheter tube 12 has a single lumen 14.

Figure 10:
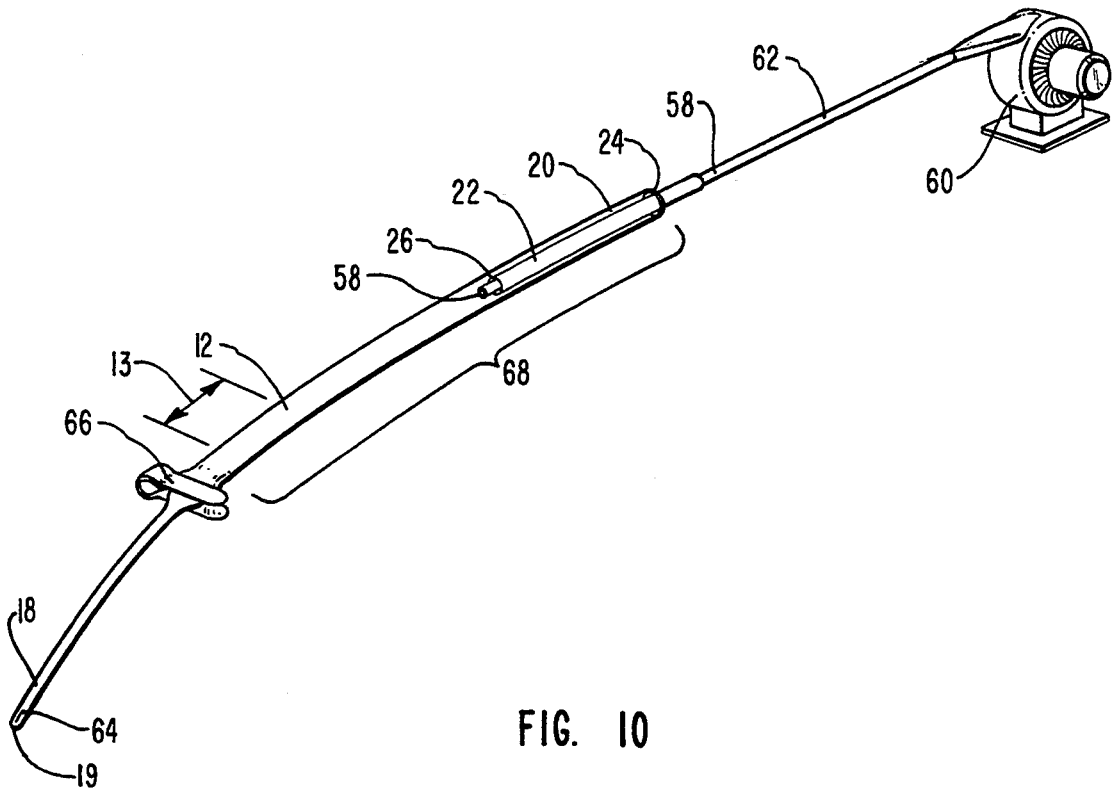
FIG. 10 is a perspective view of the apparatus used in the "pressurized gas" method of the present invention to produce the inventive catheter.

In addition, as shown in FIGS. 5, 6, and 10 catheter tube 12 may have a valve 64 located at the distal end 18 thereof. Proximal end 20 of catheter tube 12 is open. The edges of valve 64 remain in abutment and closed in a normal state. The valve 64, however, responds to pressure differentials and the edges thereof will disengage to create an opening, so that materials may pass through two-way valve 64 into or out of lumen 14. Thus valve 64 is capable of assuming three distinct positions, a first that is closed to all fluid flow, a second that permits fluid flow outwardly from the lumen of catheter tube 13, and a third that permits fluid flow inwardly into the lumen of catheter tube 12. Nevertheless, for convenience hereinafter a valve, such as valve 64, which can assume three positions can also be characterized by the two opposite directions in which such a valve permits a flow of fluid and will thus for convenience hereafter on occasion be referred to as a "two-way" valve.

If inventive catheter 10 is implanted through the subclavian vein of a patient, inventive catheter 10 will traverse the triangular space bounded by the clavicle and first rib anteriorly and the anterior scalene muscle posteriorly. This space is the "pinch-off region" discussed above. There, within the subclavian vein, inventive catheter 10 will be subjected to repeated intermittent compressive and abrasive forces.

If inventive catheter 10 is inserted using the percutaneous subclavian route so as to pass medial of the subclavian vein in the space bounded by the costo-clavicular ligament in the angle between the first rib and clavicle, anteriorly and outside of the subclavian vein posteriorly, the inventive catheter 10 will be particularly vulnerable to the imposition thereupon of repeated intermittent compressive and abrasive forces from the pincher-like movement of the clavicle against the first rib.

In either case, the portion of implanted inventive catheter 10 that is exposed to these pressures in the "pinch-off region" can become heavily worn during the implantation period. That portion of catheter 10 will, thus hereinafter be referred to as a "wear region" along the length of inventive catheter 10. In general it is an object of the present invention that the wear region coincide with region 13 illustrated in FIG. 1.

According to one aspect of the present invention, in order to enhance the durability of catheter tube 12, inventive catheter 10 is provided with safety means site-selectively located within lumen 14 of catheter 12 at the wear region for permitting fluid flow in the lumen when the wear region is free of the intermittent forces in the "pinch-off region," for yielding with the catheter when the wear region is subjected to those intermittent pressures, and for maintaining the integrity of lumen 14 and the physical interconnectedness of the distal and proximal ends of catheter tube 12 following any fracture or severance thereof at the wear region due to the action of those intermittent forces.

As shown by way of example and not limitation, a flexible nonmetallic inner sleeve 22 having a proximal end 24 and a distal end 26 is inserted site-selectively within catheter tube 12 to wear region 13. Nonmetallic inner sleeve 22 is tubular in structure, so that nonmetallic inner sleeve 22 does not present an obstacle to the flow of fluids passing through lumen 14 of catheter tube 12. The passage of these fluids is critical to a patient. Nonmetallic inner sleeve 22 prevents the integrity of the lumen in catheter tube 12 from becoming compromised when catheter tube 12 is partially or totally separated at inner sleeve 12 due to compressive forces generated by the body of a patient.

Other structural features of nonmetallic inner sleeve 22 enable a generally unimpaired flow of fluid through lumen 14. In one embodiment of the present invention, proximal end 28 and distal end 30 of nonmetallic inner sleeve 22 have chamfered edges 30 at each end of lumen 34 therethrough. The chamfered edges 30 conform nonmetallic inner sleeve 22 to the configuration of the inside of lumen 14 of catheter tube 12 to allow materials to travel unhindered through inventive catheter 10.

Nonmetallic inner sleeve 22 can be comprised wholly of a single type of material or of different substances. In a preferred embodiment of the present invention, nonmetallic inner sleeve 22 is comprised of polyurethane. This material is compressible, but also resistant to separation by compressive forces and maintains its conformational integrity in the force thereof. Additionally, this material will permit catheter tube 12 with inner sleeve 22 disposed therein to easily follow and conform to the normal insertion route in the body of a patient for catheter 10 without causing injury to surrounding body tissues. In other embodiments, nonmetallic inner sleeve 22 has been comprised of tetrafluoroethylene or fluorinated ethylene propylene. The present invention, however, is not limited to these constructions.

Nonmetallic inner sleeve 22 has an outer diameter that is greater than the inner diameter of catheter tube 12. Thus, when nonmetallic inner sleeve resides in lumen 14 of catheter tube 12, the inner walls of catheter tube 12 frictionally engage the exterior of nonmetallic inner sleeve 22. It is this frictional engagement that maintains the position of nonmetallic inner sleeve 22 relative to catheter tube 12.

Due to the frictional engagement between the exterior of nonmetallic inner sleeve 22 and the interior of catheter tube 12, the embolization of any portion of catheter tube 12 in the body of a patient is prevented. Should the distal end 18 and proximal end 20 of catheter tube 12 partially or totally separate because of the previously mentioned compressive forces, the frictional engagement exerted on inner sleeve 22 by each prevents the extravasation of infusates and keeps the severed portions of catheter tube 12 from separating. Therefore, nonmetallic inner sleeve 22 maintains a constant connection between fractured or separated portions of catheter tube 12.

It is important to reemphasize that nonmetallic inner sleeve 22 is disposed within lumen 14 of catheter 12. Positioning a sleeve on the outside of catheter tube 12 could be done by stretching the ends of catheter tube 12 slightly to reduce the outer diameter of catheter tube 12 so that the nonmetallic outer sleeve could be slid into position about catheter tube 12.

This structural arrangement is however undesirable. Nonmetallic inner sleeve 22 does not prevent stresses or distortions from being transmitted to catheter tube 12 when the two are disposed adjacent each other. Thus, should the catheter with an outer sleeve be subjected to compressive forces, catheter tube 12 will still eventually partially or totally separate. Thereafter, when catheter tube 12 is removed from a patient by the most common removal procedure of pulling on the proximal end 20, catheter tube 12 will stretch and pull out of any nonmetallic inner sleeve. Then the nonmetallic inner sleeve and the distal end of catheter 12 would be left within the body of the patient. As previously discussed, once the compressive forces about nonmetallic inner sleeve 22 are relieved by body movement, the these portions can be quickly carried into the heart. The resulting embolus can cause heart arrhythmias, and be a focal point for very serious infection in the cardiovascular system.

The structural arrangement of the present invention prevents any such dangers from occurring to a patient. With nonmetallic inner sleeve 22 disposed within catheter tube 12, totally separated sections of catheter tube 12 cannot be pulled off of nonmetallic inner sleeve 22. This is due to the elongation and necking down of catheter tube 12, making catheter tube 12 even tighter on nonmetallic inner sleeve 22, increasing the frictional interface between the catheter tube 12 and nonmetallic inner sleeve 22.

The outer diameter of nonmetallic inner sleeve 22 needs to be large enough to frictionally interface with the inner diameter of catheter tube 12.

In one embodiment of the present invention the inner diameter of catheter tube 12 is in the range of from about 0.055 inches to about 0.066 inches. The outer diameter of nonmetallic inner sleeve 22 is in the range of from about 0.071 inches to about 0.077 inches. Nevertheless, the present invention is not limited to these dimensions.

In one embodiment of the present invention, nonmetallic inner sleeve 22 is positioned in the range of from about one inch to about two feet from distal end 18 of catheter tube 12. In the most preferred embodiment, however, nonmetallic inner sleeve 22 is positioned about 1.5 inches from distal end 18 of catheter tube 12.

The length of nonmetallic inner sleeve 22 is in one embodiment of the present invention in the range from about 8 inches to about 8.5 inches. In the most preferred embodiment, however, nonmetallic inner sleeve 22 is about 8.25 inches in length.

Figure 3:
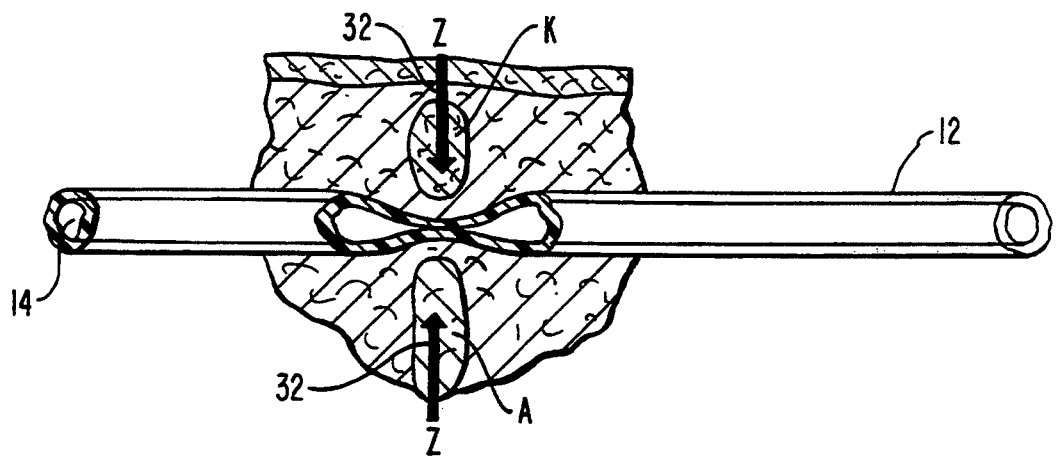
FIG. 3 is a side view in the partial break-away of a prior art catheter subjected to compressive body forces.

FIG. 3 illustrates the effect of compressive forces on a prior art catheter tube 12 that is not enhanced by any inner sleeve 22. Compressive forces 32 from first rib A and clavicle K are directed toward each other as indicated by arrows Z. In this way catheter tube 12 in FIG. 3 is distorted. Repeated infliction of compressive forces 32 on the outer surface of catheter tube 12 will wear down the body of catheter 12. Eventually, the body of catheter tube 12 becomes brittle or worn, and partially or totally separated.

Figure 4:
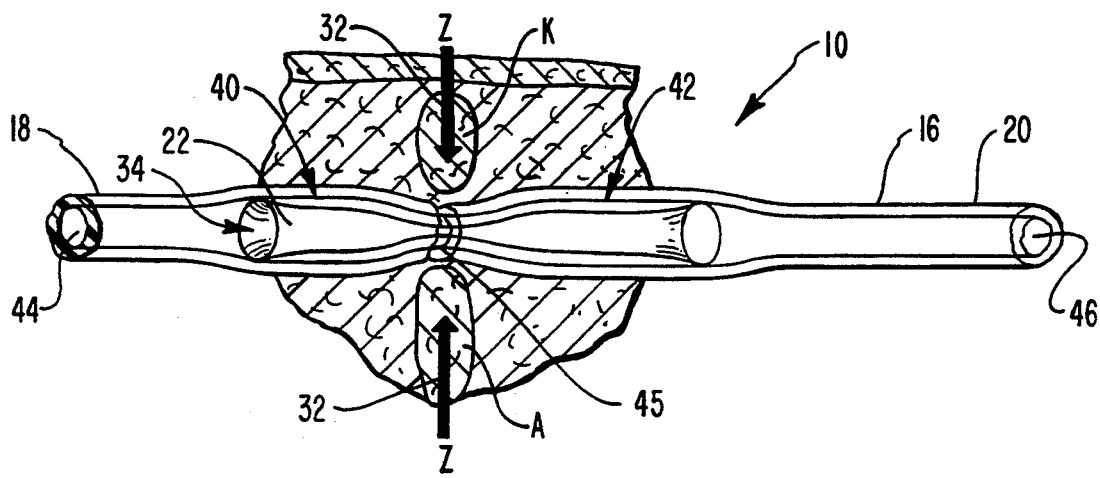
FIG. 4 is a side view in partial break-away of the inventive catheter of FIG. 2, illustrating the catheter after being totally separated into two parts due to compressive body forces.

FIG. 4 illustrates how inventive catheter 10 reacts to compressive forces 32. FIG. 4 contains a cut-away view of lumen 34 of nonmetallic inner sleeve 22 which changes its shape when compressive forces 32 engage inventive catheter 10. Likewise, lumen 14 of catheter tube 12 changes its conformation. As it will be more thoroughly discussed at a future point, however, catheter tube 12 remains in frictional engagement with nonmetallic inner sleeve 22, even if compressive forces 32 partially or totally separate the opposite ends of catheter tube 12.

Because nonmetallic inner sleeve 22 is slightly larger than lumen 14 of catheter tube 12, the body of catheter tube 12 must be expanded to accept nonmetallic inner sleeve 22. Once nonmetallic inner sleeve 22 is positioned within catheter tube 12, the body of catheter 12 attempts to regain its non-expanded conformation and presses inwardly on nonmetallic inner sleeve 22. This result has the effect of keeping nonmetallic inner sleeve 22 in place within lumen 14 of catheter tube 12. In this way, once positioned to counteract generated compressive forces 32, nonmetallic inner sleeve 22 will stay in the same place within catheter tube 12.

An additional benefit from the body of catheter tube 12 pressing against nonmetallic inner sleeve 22 is that, if the body of catheter 12 around nonmetallic inner sleeve 22 is worn away by the continued imposition of compressive forces 32, nonmetallic inner sleeve 22 continues to serve as a connector body between the severed portions of the catheter body. This benefit is better illustrated by reference to FIG. 4, wherein catheter tube 12 resides in the area of a patient between the clavicle K and the first rib A which generates compressive forces 32. Due to compressive forces 32, catheter tube 12 has become separated into two distinct parts by a gap 45.

In FIG. 4, gap 45 separates catheter tube 12 into a first section 40 and a second section 42. The tubular structure of nonmetallic inner sleeve 22 extends the communication between the lumen 44 of first section 40 and the lumen 46 of second section 42. Gap 45 is narrow as illustrated in FIG. 4. This may not, however, be the case in all instances.

The connection between first section 40 and second section 42 results because the outer diameter of nonmetallic inner sleeve 22 is slightly larger than the inner diameter of catheter tube 12. Thus, when nonmetallic inner sleeve 22 resides within lumen 14 of catheter tube 12, catheter tube 12 presses and frictionally engages the exterior of nonmetallic inner sleeve 22. Thereafter, should separation of the catheter wall occur, first section 40 and second section 42 of catheter tube 12 remain in frictional engagement with nonmetallic inner sleeve 22, which continues to provide the communication between lumen 44 of first section 40 and lumen 46 of second section 42. Inner sleeve 22 itself resists any wear by the compressive and abrasive forces.

The selective site enhancement of an implanted catheter to compensate for specific areas of compressive stress imposed by the body of a patient should not be confused with the binding of a catheter along most or all of its length to increase the torsional rigidity of the catheter or to prevent its compression. Compression involves the squeezing together of a section of the catheter. Catheter separation and embolization occur as a result of long-term intermittent compression imposed on the body of the catheter. Torsion, on the other hand, involves the twisting of the catheter by the exertion of forces tending to turn one end or part about a longitudinal axis while the other is held fast or turned in the opposite direction. In the present invention, it is compressive forces relative which the inventive catheter is enhanced, and the safety means thereof compensates for the wear imposed by those forces. Nevertheless, the area of site-selective reinforcement is only slightly more torsionally resistant than the rest of the length of the catheter tube. Attempts have been made to increase the torsional rigidity of catheters by taking a tubular structure and forming a catheter body around the tubular structure. The dual-body structure of the resulting catheter by this "after-forming" procedure increases the torsional rigidity of the structure. Often the tubular structure of the after-formed catheter body has been comprised of such rigid materials such as metals, but torsional or compressive rigidity in any major degree is contrary to the teachings of the present invention.

In the present invention, nonmetallic inner sleeve 22 is inserted within a catheter which has already been formed, and therefore inventive catheter 10 is quite different from a catheter created by the after-formed procedure. Nonmetallic inner sleeve 22 is site-selectively positioned within catheter 12 to cope with the consequences of compressive forces 32. Nonmetallic inner sleeve 22 does not substantially increase the torsional rigidity of catheter 12, as would a metallic reinforcement in an after-formed catheter.

Moreover, the differences between an after-formed catheter and a catheter with a nonmetallic inner sleeve 22 can be further understood by a further examination of their methods of manufacture. The after-formed catheter is formed by molding an outer layer around a tubular structure.

The present application contemplates two methods that have been used to manufacture inventive catheter 10. These are the "chemical soak" method, and the "pressurized gas" method. Both methods vary greatly from the method of manufacturing an after-formed catheter.

The chemical soak method can be understood with reference first to FIG. 5, which illustrates the first step of the chemical soak method. This involves exposing a length of catheter tube 12 to a chemical compound which causes the exposed portion of catheter tube 12 to swell.

This chemical treatment step causes lumen 14 of catheter tube 12, which before the chemical treatment was of a diameter smaller than nonmetallic inner sleeve 22, to expand to a diameter greater than nonmetallic inner sleeve 22. This result allows nonmetallic inner sleeve 22 to be slidably advanced within lumen 14 of catheter tube 12. As illustrated in FIG. 5, catheter tube 12 has an open proximal end 20 and a distal end 18 that terminates in a closed distal tip 19. Catheter tube 12 is provided with a two-way valve 64 that is responsive to pressure differentials and is therefore capable of permitting the ingress and egress of fluids into and from fluid accommodating lumen 14.

Because it is implicit in the invention that part of catheter tube 12 be enhanced relative to the long-term effects of compressive forces 32, at least that part of catheter tube 12 must therefore be immersed in the chemical and expanded so nonmetallic inner sleeve 22 can be placed therewithin. As it can be seen in FIG. 5, those portions of catheter 12 through which nonmetallic inner sleeve 22 will be slid from proximal end 20 also needs to be immersed in the chemical in order for nonmetallic inner sleeve 22 to travel from the inserted end to the site-selective position at region 13.

It is important to note that because nonmetallic inner sleeve 22 can be inserted in any expanded opening, and catheter tube 12 has proximal end 20 and distal end 18, an option exists for nonmetallic inner sleeve 22 to be inserted through an opening at the distal end of the catheter tube, if the distal tip of the catheter is open. This cannot occur, relative to catheter tube 12 however, as a two-way valve 64 is provided at the distal end 18 thereof, only if distal tip 19 is closed. Therefore, in the embodiment of the present invention, illustrated in FIG. 5 nonmetallic inner sleeve 22 is inserted through the open expanded proximal end 20 of catheter tube 12.

The chemical which has been found to have catheter expanding capabilities and is the chemical employed in the preferred embodiment of the chemical soak method is freon. Freon is naturally a liquid at room temperature, but has a high vapor pressure (affinity to become gas). The application of liquid freon causes the walls of catheter 12 to swell as the freon is absorbed.

It is the high vapor pressure of freon that allows catheter 12 to return to its normal size. The freon contained in the walls of catheter 12 evaporates, and the swelling is reduced. The use of freon to alter the size of the diameter of catheter tube 12 is beneficial, because freon does not leave a residue upon evaporation. Freon is not the only chemical that has catheter expanding capabilities, and the present invention is not intended to comprise only the use of freon in this regard. It has been noted that cyclohexanone, methyl ethyl ketone, and isopropyl alcohol may also be employed in the present invention. The foregoing are provided as examples, and are not meant to limit the scope of the chemicals having catheter expanding capabilities that may be employed in the present invention.

As illustrated in FIG. 5, freon 48 is placed in a container 50 and then a portion of catheter 12 including region 13 is exposed to freon 48. In one embodiment of the present invention, catheter tube 12 is exposed to freon 48 for a duration of from about one to about ten minutes. In the preferred embodiment of the present invention, catheter tube 12 is exposed to freon 48 for at least about five minutes.

FIG. 6 illustrates the effect the chemical treatment has upon catheter tube 12 after exposure to freon 48. Expanded portion 52 of catheter tube 12 exposed to the chemical treatment is enlarged in relation to the portions of catheter tube 12 not exposed to the chemical treatment. The chemical is absorbed in the walls of catheter tube 12, and results in swelling. Because the body of catheter tube 12 is expanded in diameter, lumen 14 of catheter tube 12 is likewise increased in diameter to a diameter greater than that of nonmetallic inner sleeve 22.

Once lumen 14 of expanded portion 52 of catheter tube 12 immersed in the chemical is capable of accepting nonmetallic inner sleeve 22, nonmetallic inner sleeve 22 is advanced through lumen 14 of expanded portion 52 of catheter tube 12 to region 13, which will experience compressive forces 32. Nonmetallic inner sleeve 22 has an outer diameter greater than the inner diameter of catheter tube 12 before catheter tube 12 is exposed to a chemical compound, but smaller than the inner diameter of catheter tube 12 thereafter.

To accomplish this end, nonmetallic inner sleeve 22 is placed on one end of a rod 54 as shown in FIG. 7. Then rod 54 and therefore nonmetallic inner sleeve 22 are advanced within lumen 14 of catheter tube 12 in the direction indicated by arrow Y of FIG. 7.

Because the expansive nature of catheter tube 12 allows nonmetallic inner sleeve 22 to be inserted within catheter tube 12, nonmetallic inner sleeve 22 can be advanced by rod 54 throughout exposed portion 52 of catheter tube 12, until nonmetallic inner sleeve 22 becomes positioned at the selected site in region 13. In FIG. 8, nonmetallic inner sleeve 22 is shown having been inserted through lumen 14 of catheter tube 12 to a site-selected position in region 13. Nonmetallic inner sleeve 22 is not, however, able to enter that portion of catheter tube 12 beyond exposed portion 52, as that portion of catheter tube 12 has not been immersed in freon 48. Therefore, the portion of catheter tube 12 beyond exposed portion 52 has an inner diameter that is smaller than the outer diameter of nonmetallic inner sleeve 22.

As also shown in FIG. 8, once nonmetallic inner sleeve 22 has been positioned at a desired site, rod 54 may be withdrawn from nonmetallic inner sleeve 22 in the direction shown by arrow Y'. Nonmetallic inner sleeve 22 is left in the site selected position in region 13 that is subject to compressive forces 32.

Finally, the chemical soak method comprises the step of drying expanded portions 52 of catheter tube 12 exposed to the chemical compound, thereby to return expanded portions 52 of catheter tube 12 the original size thereof. This leaves nonmetallic inner sleeve 22 within lumen 14 of catheter tube 12 in frictional engagement with the interior thereof. Catheter tube 12 having nonmetallic inner sleeve 22 within lumen 14 of catheter 12 is thereafter enhanced in the durability thereof relating to compressive forces 32, thereby to prevent possible partial or total separation of catheter tube 12.

As the chemically exposed areas of catheter tube 12 interact with air, the portions of catheter tube 12 exposed to freon 48 gradually return to the original size thereof. This result occurs because of the high vapor pressure of the freon. Due to the affinity of the freon to become gas, the freon quickly evaporates from the walls of catheter tube 12 which are thereby reduced in swelling.

Because the original size of the inner diameter of catheter tube 12 is smaller than the size of the outer diameter of nonmetallic inner sleeve 22, catheter tube 12 presses against and fixedly secures nonmetallic inner sleeve 22 within lumen 14 of catheter tube 12. The structure of the thusly completed inventive catheter 10 is illustrated in FIG. 9.

The catheter of the present invention can also be produced by a pressurized gas method which can be understood first by reference to FIG. 10. In this method nonmetallic inner sleeve 22 is placed on one end of a hollow rod 58 which is connected to a pressurizing gas source 60. Nonmetallic inner sleeve 22 is then advanced through lumen 14 of catheter tube 12 from proximal end 20 toward distal end 18.

As shown in FIG. 10, the end of hollow rod 58, remote from nonmetallic inner sleeve 22, is connected to low volume, high pressure gas source 60 by way of an air line 62. In this manner, pressurized air is directed through the air line 62 and out of the end of hollow rod 58. It should be noted, however, that air is not the only gas which may be directed under pressure through hollow rod 58. Other gases may be employed with equal success. In the preferred embodiment of the method of the present invention, a range of air pressure from about 80 psi to 90 psi of gas is introduced thereby into lumen 14 of catheter tube 12.

Catheter tube 12 is soft-clamped by a clamp 66 at a position intermediate the desired reinforcement site in region 13 and the two-way valve 64 at distal end 18 of catheter tube 12. Otherwise, air introduced within lumen 14 at proximal end 20 of catheter 12 would escape through two-way valve 64. As a result of clamp 66, pressurized air passing through hollow rod 58 into lumen 14 slightly inflates and enlarges catheter tube 12. This allows nonmetallic inner sleeve 22 to be advanced within catheter tube 12.

Clamp 66 is referred to as "soft" in light of its structural features. Whereas most clamps have angled edges which can possibly injure a catheter, clamp 66 has rounded edges which provide a short-term compressed effect on catheter 12 to block lumen 14. Blocked lumen 14 enables hollow rod 58 to inflate and slightly enlarge the portion of catheter tube 12 between clamp 66 and proximal end 20 of catheter tube 12.

The method also comprises the step of advancing nonmetallic inner sleeve 22 to region 13 of catheter tube 12 that experiences compressive forces 32. Catheter tube 12 expands in response to the introduction of pressurized air and nonmetallic inner sleeve 22 can be advanced thereinto. The outer diameter of nonmetallic inner sleeve 22 is normally greater than the inner diameter of catheter tube 12, but expanding catheter tube 12 with the pressurized air allows nonmetallic inner sleeve 22 to be advanced through catheter tube 12.

Figure 11:
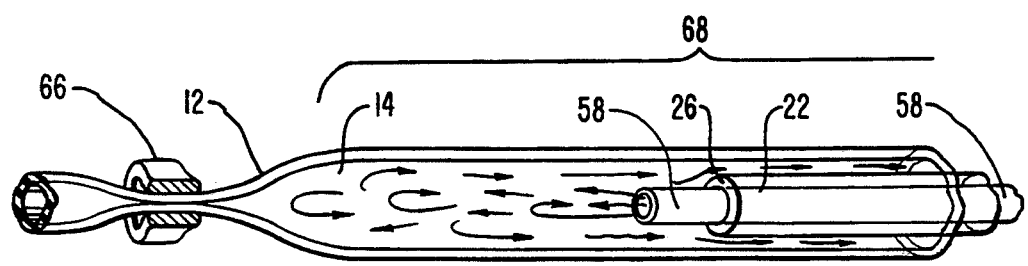
FIG. 11 is an enlarged side view of the apparatus of FIG. 10 illustrating the enlargement of the catheter lumen by pressurized air as the inner sleeve is inserted thereto.

As indicated in FIG. 11, the end of hollow rod 58 with nonmetallic inner sleeve 22 mounted thereon, is entered into and advanced along lumen 14 of catheter tube 12 from open proximal end 20 thereof. The pressurized air passing through hollow rod 58 inflates and slightly enlarges a portion 68 of catheter tube 12. Enlarged portion 68 of catheter tube 12 creates an enlarged lumen through which nonmetallic inner sleeve 22 may pass.

Figure 12:
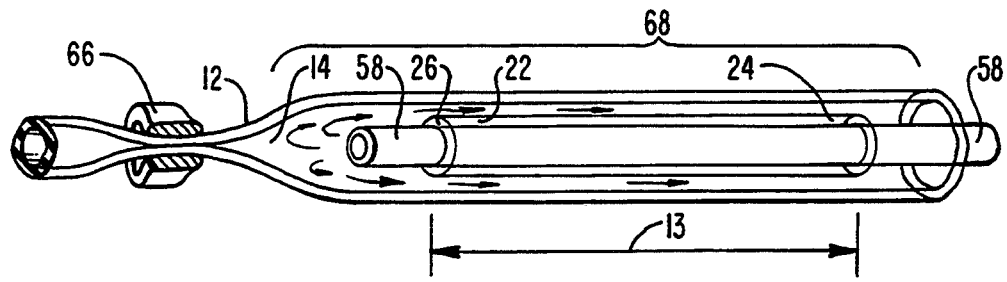
FIG. 12 is an enlarged side view of the apparatus of FIG. 10 illustrating the inner sleeve being guided by a hollow push rod to a desired position within the catheter tube.

The areas through which pressurized air passes are shown by arrows in FIGS. 11 and 12. The pressurized air passing through hollow rod 58 inflates and slightly enlarges catheter tube 12 and escapes therefrom between advancing nonmetallic inner sleeve 22 and the inner wall of catheter tube 12. As a result, nonmetallic inner sleeve 22 and hollow rod 58 are easily advanced into position in region 13 as shown in FIG. 12.

According to the pressurized gas method, air at a high pressure and controlled volume is utilized to partially inflate catheter tube 12, while at the same time providing a non-toxic, low-friction interface layer between nonmetallic inner sleeve 22 and the inner surface of lumen 14 of catheter tube 12.

In one embodiment of the present invention, a catheter having a Groshong ® valve as a two-way valve 64 may be employed. Because this type of valve is responsive to pressure differentials, there is a possibility that the Groshong ® valve could be damaged by the pressurized gas required by the method of the present invention. Therefore, as previously discussed, it is preferred that the present invention comprise the further step of soft-clamping catheter tube 12 at a position intermediate the desired reinforcement site and the two-way valve 64 at distal end 18 of catheter tube 12.

Figure 13:
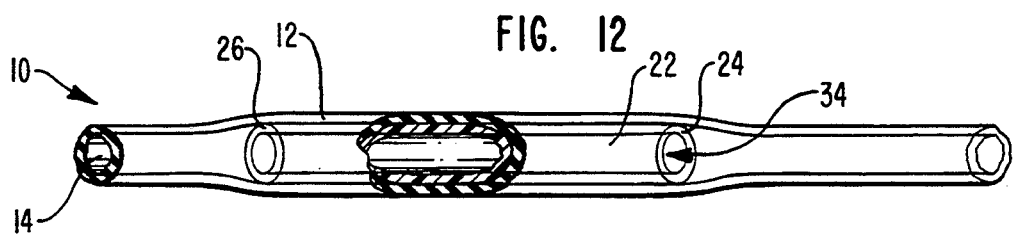
FIG. 13 is a planar side view of an inventive catheter produced by the "pressurized gas" method of the present invention after the hollow push rod has been withdrawn and the catheter tube is in frictional engagement with the inner sleeve.

Once catheter tube 12 has been soft-clamped, hollow rod 58 is used to advance nonmetallic inner sleeve 22 to a site-selective position in catheter tube 12 and is then withdrawn from nonmetallic inner sleeve 22 and catheter tube 12. Nonmetallic inner sleeve 22 is left within catheter tube 12, which returns to a normal size after hollow rod 58 has been removed. Inventive catheter 10 having nonmetallic inner sleeve 22 within lumen 14 of catheter tube 12 is shown in FIG. 13. Inventive catheter 10 has enhanced durability relative to compressive forces 32. This prevents partial catheter separation that allows for the extravasation and total catheter separation that leads to embolization.

In one embodiment of the present invention, nonmetallic inner sleeve 22 is advanced within lumen 14 of catheter tube 12 to a distance in a range from about one inch to about two feet from distal end 18 of catheter tube 12. In the preferred embodiment, however, nonmetallic inner sleeve 22 is advanced within lumen 14 of catheter tube 12 to a distance of about one and one-half inches from distal end 18 of catheter 12.

The present invention also comprises the method of using inventive catheter 10. The preferred embodiment of this method comprises those steps which comprise the methods of manufacturing inventive catheter 10. In addition, the method of using inventive catheter 10 comprises the step of implanting inventive catheter 10 within the body of a patient.

In the preferred embodiment of the present invention, inventive catheter 10 may be implanted traversing an area of the body of a patient which generates compressive pressures 32. In the most preferred embodiment, inventive catheter 10 is implanted to traverse the area of the body of a patient between the clavicle and first rib. Nevertheless, the present invention is not limited to the mentioned areas of implantation.

The implantation of inventive catheter 10 within the body of a patient can be accomplished in the same way that other catheters known to the art are implanted. Most often, implantation will involve the use of some type of system employing a needle or trocar and an introducer.

From the foregoing, it will be appreciated that the present invention provides apparatus and methods for reducing the susceptibility of implanted catheters inserted by way of the percutaneous subclavian route to damaging stresses due to body movement.

Additionally, the present invention provides apparatus and methods for enhancing the area of a catheter disposed in a region of the body subjected to damaging stresses due to body movement. This prevents embolization of the implanted catheter by maintaining a connection between stress-induced severed catheter portions should separation or fractionation occur. Frictional engagement between each of the severed catheter portions surrounding the reinforcing inner sleeve acts to maintain the connection between the severed catheter portions.

Also, the present invention provides apparatus and methods for enhancing the area of a catheter disposed in a region of the body subjected to damaging stresses due to body movement, but without a major deviation from currently existing standard practices.

Applicant's invention overcomes severe complications from partial or total catheter severance documented in the medical literature. As a result, patients requiring long-term implanted venous access systems need not be exposed to the predictable risks of catheter rupture and embolization. Catheters need not be removed prematurely to the desired term of their utility for fear of such risks. Regular chest X-rays to verify catheter integrity can be reduced and possibly omitted. In addition patients requiring implanted venous access systems need no longer be required to lose a healthy jugular vein to avoid the problems of the "pinch-off region."

The present invention provides apparatus and methods for reinforcing a catheter disposed in an area subject to damaging stresses due to body movement which will allow the insertion of a reinforcing inner sleeve which will be soft enough to easily follow and conform to the normal path of insertion through the body of a patient for the catheter, as well as preventing the integrity of the lumen of the catheter from becoming compromised as a result of the partial or total catheter separation due to the pinching action of the clavicle and first rib.

Still yet, the present invention provides apparatus and methods for enhancing the area of a catheter disposed in a region of the body subjected to damaging stresses due to body movement which is easy to handle and manipulate by medical personnel and will not harden or deteriorate over time.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. A central venous access catheter for long-term indwelling implantation in the body of a patient, the catheter when implanted traversing an anatomical pinch-off region in the body of the patient between the clavicle and the first rib that subjects the portion of the length of the catheter disposed through the anatomical region to intermittent, repeated compressive and abrasive forces, said catheter comprising:
  (a) a flexible tube comprised of a compliant medical grade material enclosing a fluid accommodating lumen extending longitudinally through substantially the entire length of said flexible tube, said flexible tube having a distal tip for residence at a preselected location within the cardiovascular system of the body of the patient when said catheter is implanted, and a proximal end through which to afford access to said fluid accommodating lumen when said catheter is implanted, the portion of the length of said flexible tube traversing the anatomical region when said catheter is implanted defining a wear region along the length of said flexible tube, said wear region being distanced from said proximal end and from said dismal tip of said flexible tube; and
  (b) safety means positioned within said fluid accommodating lumen of said flexible tube at least at said wear region and terminating proximal of said distal tip of said flexible tube
    (i) for permitting fluid flow in said lumen when said wear region is free of the compressive and abrasive forces,
    (ii) for yielding with said flexible tube when said wear region is exposed to the compressive or abrasive forces, and
    (iii) for maintaining the integrity of said lumen following the fracture or severance of said flexible tube at the wear region due to the compressive or abrasive forces.

2. A catheter as recited in claim 1, wherein said safety means comprises a flexible, resilient tubular sleeve disposed inside said lumen of said flexible tube at least at said wear region in frictional engagement with the walls of said lumen, so as to terminate proximal of said distal kip of said flexible tube.

3. A catheter as recited in claim 1, wherein said flexible tube has a single lumen.

4. A catheter as recited in claim 1, wherein said flexible tube has a closed distal tip and is provided at a position proximate thereto, but distal of said safety means, with a two-way valve.

5. A catheter as recited in claim 6, wherein said two-way valve is capable of permitting the selective ingress and egress of fluids into and from said lumen, respectively.

6. A catheter as recited in claim 2, wherein said tubular sleeve is comprised of a single type of material.

7. A catheter as recited in claim 2, wherein said tubular sleeve is comprised of a nonmetallic material.

8. A catheter as recited in claim 2, wherein said tubular sleeve is comprised of polyurethane.

9. A catheter as recited in claim 2, wherein said tubular sleeve is comprised of polyvinyl chloride.

10. A catheter as recited in claim 2, wherein said tubular sleeve is comprised of tetrafluoroethylene.

11. A catheter as recited in claim 2, wherein said tubular sleeve is comprised of fluorinated ethylene propylene.

12. A catheter as recited in claim 2, wherein said tubular sleeve has an outer diameter greater than the inner diameter of said flexible tube.

13. A central venous access catheter for long-term indwelling implantation in the body of a patient, the catheter when implanted traversing a pinch-off region in the body of the patient between the clavicle and the first rib that subjects the portion of the length of the catheter disposed through the pinch-off region to intermittent, repeated compressive and abrasive forces, said catheter comprising:
  (a) a flexible tube comprised of a compliant medical grade material enclosing a fluid accommodating lumen extending longitudinally through substantially the entire length of said flexible tube, said flexible tube having a closed distal tip for residence at a preselected location within the cardiovascular system of the body of the patient, when said catheter is implanted, a proximal end through which to afford access to said fluid accommodating lumen when said catheter is implanted, and a two-way valve responsive to pressure differentials capable of permitting the ingress and egress of fluids into and from said fluid accommodating lumen, respectively, the portion of the length of said flexible tube traversing the pinch-off region when said catheter is implanted defining a wear region along the length of said flexible tube, said wear region being distanced from said proximal end and from said distal tip of said flexible tube; and (b) a flexible, resilient tubular sleeve disposed inside said fluid accommodating lumen of said flexible tube at least at said wear region in frictional engagement with the walls of said fluid accommodating lumen so as to terminate proximal of said two-way valve.

14. A catheter as recited in claim 13, wherein said tubular sleeve is made of polyurethane.

15. A catheter as recited in claim 13, wherein said catheter is implanted within the body of a patient for a time period ranging from about ten minutes to about two years.

16. A catheter as recited in claim 13, wherein a flow of fluids may pass through the lumen of said catheter with said tubular sleeve disposed therein.

17. A catheter as recited in claim 13, wherein said flexible tube has a single lumen.

18. A catheter as recited in claim 13, wherein portions of said flexible tube will not detach from said tubular sleeve when severed at said wear region by the compressive forces.

19. A catheter as recited in claim 13, wherein said tubular sleeve is positioned in the range of from about one inch to about two feet from the distal tip of said flexible tube.

20. A catheter as recited in claim 13, wherein said tubular sleeve is positioned about three inches from the distal tip of said flexible tube.

21. A catheter as recited in claim 13, wherein said tubular sleeve has an outer diameter in a range of from about 0.071 inches to about 0.077 inches.

22. A catheter as recited in claim 13, wherein said tubular sleeve has an outer diameter of about 0.074 inches.

23. A catheter as in claim 13, wherein said tubular sleeve has a length in a range of from about 8.0 inches to about 8.5 inches.

24. A catheter as recited in claim 13, wherein said tubular sleeve has a length of about 8.25 inches.

25. A catheter as recited in claim 13, wherein said flexible tube is comprised of silicone rubber.

26. A central venous access catheter for long-term indwelling implantation in the body of a patient, the catheter when implanted traversing an anatomical pinch-off region in the body of the patient between the clavicle and the first rib that subjects the portion of the length of the catheter disposed through the anatomical region to intermittent, repeated compressive and abrasive forces, said catheter comprising:

(a) a flexible tube comprised of a compliant medical grade silicone rubber enclosing a single fluid accommodating lumen extending longitudinally through substantially the entire length of said flexible tube, said flexible tube having a distal tip for residence at a preselected location within the cardiovascular system of the body of the patient, when said catheter is implanted, and a proximal end through which to afford access to said fluid accommodating lumen when said catheter is implanted, the portion of the length of said flexible tube traversing the anatomical pinch-off region when said catheter is implanted defining a wear region along the length of said flexible tube, said wear region being distanced from said proximal end and from said distal tip of said flexible tube; and (b) a flexible resilient tubular sleeve having chamfered ends and an outer diameter greater than the inner diameter of said flexible tube, said sleeve being positioned within said fluid accommodating lumen of said flexible tube at least at said wear region in frictional engagement with said walls of said fluid accommodating lumen so as to terminate proximal of said distal tip of said flexible tube.

27. A catheter as recited in claim 13, wherein said flexible tube has a closed distal tip.

28. A catheter as recited in claim 27, wherein said flexible tube has a two-way valve at a position proximal to the distal tip thereof, but distal of said tubular sleeve, said two-way valve being capable of permitting the ingress and egress of fluids into and from said lumen, respectively.

29. A catheter as recited in claim 26, wherein said tubular sleeve has chamfered ends.

30. A catheter as recited in claim 26, wherein said tubular sleeve is comprised of polyurethane.

31. A catheter as recited in claim 26, wherein said tubular sleeve is comprised of polyvinyl chloride.

32. A catheter as recited in claim 26, wherein said tubular sleeve is comprised of tetrafluoroethylene.

33. A catheter as recited in claim 26, wherein said tubular sleeve is comprised of fluorinated ethylene propylene.

34. A catheter as recited in claim 26, wherein said tubular sleeve is positioned about three inches from said distal tip of said flexible tube.

35. A catheter as recited in claim 26, wherein said tubular sleeve has a diameter in a range of from about 0.071 inches to about 0.077 inches, and said flexible tube has an inner diameter in a range of from about 0.055 inches to about 0.066 inches.

36. A catheter as recited in claim 26, wherein said tubular sleeve has a length in a range of from about 8.0 inches to about 8.5 inches.

37. A catheter as recited in claim 26, wherein the outer diameter of said tubular sleeve is greater than the inner diameter of said flexible tube.

38. A catheter as recited in claim 2, wherein said tubular sleeve terminates distal of said proximal end of said flexible tube.

39. A catheter as recited in claim 13, wherein said tubular sleeve terminates distal of said proximal end of said flexible tube.

40. A catheter as recited in claim 26, wherein said tubular sleeve terminates distal of said proximal end of said flexible tube.

* * * * *

UNITED STATES PATENT AND TRADEMARK OFFICE
CERTIFICATE OF CORRECTION

PATENT NO. : 5,389,091
DATED : February 14, 1995
INVENTOR(S) : H. ROBERT MOORHEAD It is certified that error appears in the above-indentified patent and that said Letters Patent is hereby corrected as shown below:

```
      Column 1, line 10, "Moorhead" should be --Moorehead--
      Column 5, line 10, "break-after" should be --break after--
      Column 9, line 27, "all initial" should be --an initial--

Column 15, lines 3-9, --As illustrated in FIG. 5, catheter
tube 12 has an open proximal end 20 and a distal end 18 that
terminates in a closed distal tip 19.  Catheter tube 12 is provided
with a two-way valve 64 that is responsive to pressure differentials
and is therefore capable of permitting the ingress and egress of
fluids into and from fluid accommodating lumen 14-- should be
placed at column 14, line 64, after the word "swell."
      Column 20, line 4, "dismal" should be --distal--
      Column 20, line 25, "kip" should be --tip--
```

Signed and Sealed this

Twelfth Day of September, 1995

Attest:

BRUCE LEHMAN

*Attesting Officer*     *Commissioner of Patents and Trademarks*